(12) United States Patent
Li et al.

(10) Patent No.: US 8,718,353 B2
(45) Date of Patent: May 6, 2014

(54) RETICLE DEFECT INSPECTION WITH SYSTEMATIC DEFECT FILTER

(75) Inventors: Bing Li, Milpitas, CA (US); Weimin Ma, Fremont, CA (US); Joseph M. Blecher, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 7 days.

(21) Appl. No.: 13/486,253

(22) Filed: Jun. 1, 2012

(65) Prior Publication Data

US 2013/0236084 A1    Sep. 12, 2013

Related U.S. Application Data

(60) Provisional application No. 61/608,445, filed on Mar. 8, 2012, provisional application No. 61/621,725, filed on Apr. 9, 2012.

(51) Int. Cl.
  *G06K 9/00* (2006.01)
(52) U.S. Cl.
  USPC .......................................... 382/144; 382/141
(58) Field of Classification Search
  USPC .......................................... 382/141, 144, 152
  See application file for complete search history.

(56) References Cited

U.S. PATENT DOCUMENTS

| 7,283,659 B1 * | 10/2007 | Bakker et al. ................. 382/149 |
| 7,355,693 B2 | 4/2008 | Takeda et al. |
| 2009/0052765 A1 * | 2/2009 | Toyoda et al. ................ 382/149 |
| 2009/0220142 A1 * | 9/2009 | Matsushita et al. ........... 382/149 |
| 2010/0119144 A1 * | 5/2010 | Kulkarni et al. .............. 382/149 |

FOREIGN PATENT DOCUMENTS

| EP | 1156321 A1 | 11/2001 |
| RU | 1786406 C | 1/1993 |
| SU | 1167620 A1 | 7/1985 |

OTHER PUBLICATIONS

"International Application Serial No. PCT/US2013/029795, Search Report and Written Opinion mailed Jun. 14, 2013", 6 pgs.

* cited by examiner

*Primary Examiner* — Edward Park
(74) *Attorney, Agent, or Firm* — Kwan & Olynick LLP

(57) ABSTRACT

A stream of defect data is received from a reticle inspection system. The defect data identifies defects that were detected for a plurality of different portions of a reticle. Before reviewing the defect data to determine whether the reticle passes inspection and as the stream of defect data continues to be received, some of the defects are automatically grouped with other most recently one or more received defects so as to form groups of substantially matching defects. Before reviewing the defect data to determine whether the reticle passes inspection and after all of the defect data for the reticle is received, one or more of the groups of defects that have a number above a predetermined threshold are automatically filtered from the defect data so as to form filtered defect data. The filtered defect data may then be provided to a review station for determining whether the reticle passes.

26 Claims, 8 Drawing Sheets

RETICLE DEFECT INSPECTION WITH SYSTEMATIC DEFECT FILTER

CROSS-REFERENCE TO RELATED APPLICATIONS

This application claims the benefit of the following prior applications: (i) U.S. Provisional Application No. 61/608,445, filed Mar. 8, 2012, titled "Reticle Defect Inspection with Systematic Defect Filter" by Bing Li et al. and (ii) U.S. Provisional Application No. 61/621,725 filed Apr. 9, 2012, titled "Reticle Defect Inspection with Systematic Defect Filter" by Bing Li et al., which applications are herein incorporated by reference in their entirety for all purposes.

TECHNICAL FIELD OF THE INVENTION

The invention generally relates to a field of reticle inspection. More particularly the present invention relates to a method to filter systematic defects from the reticle defect detection.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication process.

After fabrication of each reticle or group of reticles, each reticle is typically inspected by illuminating it with light emanating from a controlled illuminator. A test image of a portion of the reticle is constructed based on the portion of the light reflected, transmitted, or otherwise directed to a light sensor. Such inspection techniques and apparatus are well known in the art and are embodied in various commercial products such as many of those available from KLA-Tencor Corporation of Milpitas, Calif.

During a conventional inspection process, the test image of the reticle is typically compared to a baseline image. Typically, the baseline image is either generated from the circuit pattern data or from an adjacent die on the reticle itself. Either way, the test image features are analyzed and compared with features of the baseline image. Each difference value is then compared with a predetermined threshold value. If the test image varies from the baseline image by more than the predetermined threshold, a defect is defined and reported.

Each difference detected between two images has the potential of resulting in a printable defect. Conversely, some of the detected defects will have no effect on the resulting integrated circuit. Depending on whether this threshold is set too high or two low, this technique can fail to capture small defects and can also capture a high number of "false" defects.

There is a continuing need for improved inspection techniques to accurately and reliably detect defects on reticles or the like, while reducing the number of detected "false" defects.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting a photolithographic reticle is disclosed. A stream of defect data is received from a reticle inspection system, wherein the defect data identifies a plurality of defects that were detected for a plurality of different portions of the reticle. Before reviewing the defect data to determine whether the reticle passes inspection and as the stream of defect data continues to be received, some of the defects are automatically grouped with other most recently one or more received defects so as form groups of substantially matching defects. Before reviewing the defect data to determine whether the reticle passes inspection and after all of the defect data for the reticle is received, one or more of the groups of defects that have a number above a predetermined threshold are automatically filtered from the defect data so as to form filtered defect data. The filtered defect data may then be provided to a review station for determining whether the reticle passes.

In a specific implementation, reviewing the defect data to determine whether the reticle passes inspection is performed manually. In another embodiment, the defect data is received one defect image at a time and automatically grouping is accomplished by determining whether each defect image, as it is received, matches an existing seed group if present and adding such defect image to such matching existing seed group. Otherwise, a new seed group comprising such defect image is formed. In a further aspect, determining whether each defect image matches an existing seed group if present and adding such defect image to such matching existing seed group is accomplished by comparing such defect image to a plurality of seed groups one at a time until a match is found if present. In another aspect, comparing such defect image to a plurality of seed groups one at a time until a match is found if present is accomplished by first determining whether such defect image has a substantially matching shape as a one of the seed groups and only if there is a substantially matching shape, comparing pixel-by-pixel such defect image to the seed group with the substantially matching shape. In yet a further aspect, it is determined that such defect image is grouped with a particular one of the seed groups when the pixel-by-pixel comparison results in less than a 2 by 2 pixel difference.

In another implementation, automatically grouping is accomplished in a temporal order of last to first received defect data. In another aspect, automatically grouping and filtering is performed without human intervention. In another example, the predetermined threshold has an adjusted value that depends on a level of uniformity of an area that surrounds the defect of such particular group. In a further aspect, the predetermined threshold has an adjusted value that is set so that a particular group is not filtered if such particular group's defect is surrounded by a substantially blank background. In yet a further aspect, the predetermined threshold has an adjusted value that is higher for a first group that has a 1 dimensional defect than a second group that has a two dimensional defect. In a specific implementation, the predetermined threshold for a particular group's defect type is proportional to $1/\log(A)$, wherein A is an area of unique background pattern.

In certain embodiments, the invention pertains to a system for inspecting a photolithographic reticle. The system includes at least one memory and at least one processor that are configured to perform at least some of the above described operations. In other embodiments, the invention pertains to computer readable media having instructions stored thereon for performing at least some of the above described operations.

These and other aspects of the invention arc described further below with reference to the figures.

DETAILED DESCRIPTION OF EXAMPLE EMBODIMENTS

Figure 1A:
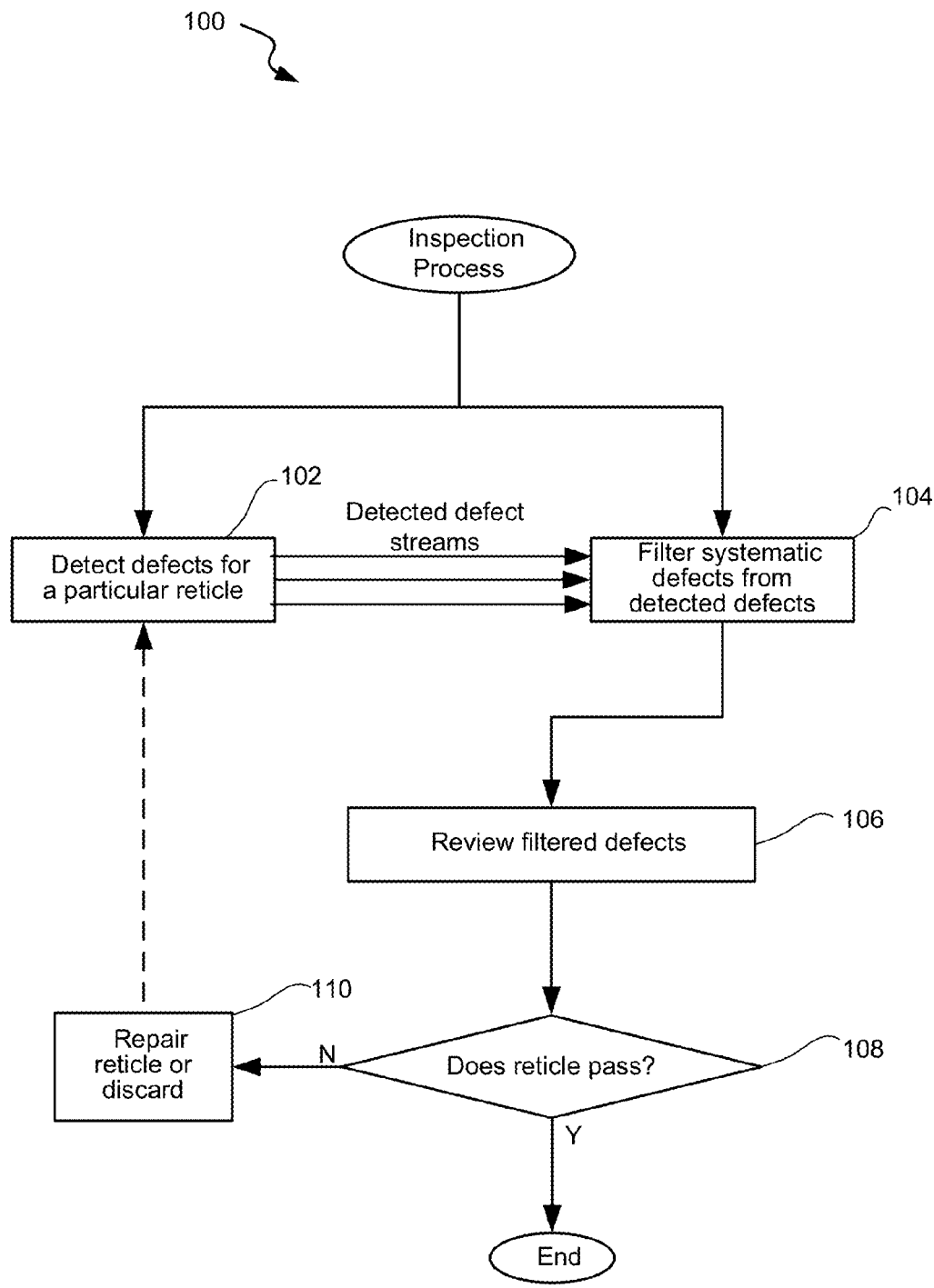
FIG. 1A is a flow chart illustrating an inspection process in accordance with on embodiment of the present invention.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

The terms "reticle" generally includes a transparent substrate such as glass, borosilicate glass, and fused silica having a layer of opaque material formed thereon. The opaque regions may be replaced by regions etched into the transparent substrate.

Many different types of reticles are known in the art, and the term reticle as used herein is intended to encompass all types of reticles. For example, the term reticle refers to different types of reticles including, but not limited to, a clear-field reticle, a dark-field reticle, a binary reticle, a phase-shift mask (PSM), an alternating PSM, an attenuated or halftone PSM, and a ternary attenuated PSM. A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs). If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

In general, detected reticle defects, which are produced during a defect detection process, can be classified into three types: real defects, rendering process defects, and reticle inspection process defects. Real defects correspond to actual contamination on a portion of the reticle or inadvertent removal of a portion of the reticle pattern. As used herein, the term "real" or "actual" defect refers to a defect in a design pattern of a reticle that may cause a defect in a design pattern printed on a wafer using the reticle, such as excessive corner rounding, unsatisfactory dimensions, missing features, bridging between features, etc. Reticle inspection process defects are induced by the inspection process. For example, the detect detection process may include a modeling process that results in "false" defects being found throughout the reticle image. Rendering process defects are introduced by the effects from the optical inspection tool. Various optical distortions can introduce differences in the reticle image that may be inadvertently detected as a defect.

False defects may also be referred to as "systematic" defects since both types of false defects are typically produced in systematic patterns or high numbers during the defect detection process. For instance, modeling introduced false defects tend to occur at the same pattern over and over again, such as high curvature patterns, or small features. In contrast, real defects are typically random events, such that the location and appearance of real defects are random and not repetitive.

FIG. 1A is a flow chart illustrating an overview of an inspection process 100 in accordance with on embodiment of the present invention. In operation 102, defects are detected for a particular reticle. In general, any suitable type and number of defect detection techniques may be implemented with embodiments of the present invention. For example, different defect detectors can be used for detecting different types of real defects, such as pinhole defects, pindot defects, different types of line edge detects, line end defects, different sized defects, contamination defects, halftone defects, etc.

Additionally, the sensitivity for detecting a particular type of defect (or all "real" defects on the reticle) can be adjusted so as to capture substantially all of the particular type of defect. In general, test reticles having different types of defects can be fabricated and then inspected to determine the sensitivity for each defect detector technique. However, the systematic defect filtering process of the present invention can be used with any suitable detected defect data and does not depend on how such data was produced.

As defects for a particular reticle are detected, one or more streams of detected defect data may be sent to a process for automatically filtering systematic defects from the detected defects in operation 104. The systematic filter process 104 can generally be configured to automatically analyze defect data as it is received by comparing one or more defects to previously received defects so as to determine whether there are patterns of similar defects being detected by grouping such matching defects together. After substantially all of the detected defect data for a particular reticle are found and grouped (if matching), the filtering process can then automatically filter the systematic defects from the detected data as described further below.

After the systematic defects are filtered from all the detected defects, the filtered defects may then be reviewed in operation 106. For example, the filtered defects may be manually reviewed to determine whether the remaining defects will likely, critically affect the operation of the fabricated device structures that are to be fabricated with the examined reticle.

It may then be determined whether the reticle passes in operation 108. This determination may be based on any suitable factor, such as number of total defects (after filtering), total number of certain types of defects, etc. If the reticle passes, the reticle may then be used to fabricate a wafer having semiconductor devices. Otherwise, the reticle is either repaired or discarded in operation 110. If the reticle is repaired, the defect detection, filtering, and review processes may then be repeated for the repaired reticle. If the reticle is discarded, another improved reticle is manufactured based on the defect results, and the defect detection, filtering, and review processes are then performed on this improved reticle.

Any suitable technique may be used for automatically filtering patterns of substantially similar defects from the detected defect data. In one implementation, defect data is analyzed in a stream of temporally sequential data so as to obtain a unique solution of defect groups that are then filtered based on number of defects in each group. Of course, other techniques may be used to obtain a unique set of grouped defects.

Figure 1B:
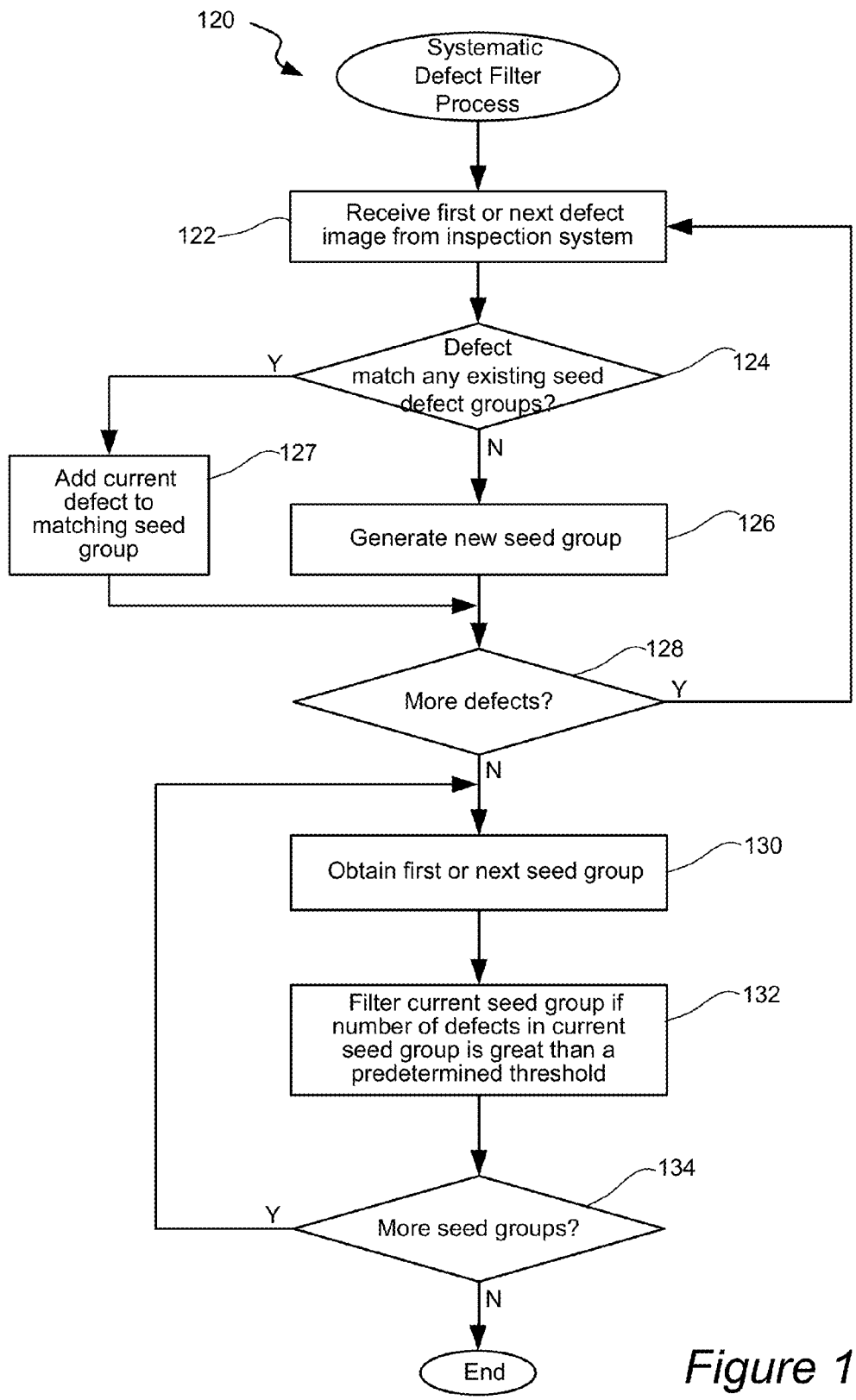
FIG. 1B is a flowchart illustrating an automatic systematic defect filtering process in accordance with a specific implementation of the present invention.

FIG. 1B is a flowchart illustrating an automatic systematic defect filtering process 120 in accordance with a specific implementation of the present invention. In this example, defect data is grouped in a temporal order. Initially, a first defect image is received from an inspection system in operation 122. In this embodiment, as each defect is found, the defect image (or signal or data) is obtained by an automatic filtering process. As described further below, the reticle can be scanned to obtain a plurality of images that are individually processed by a plurality of image processors that analyze the images to detect defects. As each defect is found, the filtering process can then receive a defect image corresponding to such found defect.

After a first defect image is received, it may then be determined whether the received defect image matches any existing seed defect groups in operation 124. Since this the first defect image, it is determined that there is no match. A new seed group is then generated based on the current defect image in operation 126. It may then be determined whether there are any more defects in operation 128. In other words, it is determined whether all of the defect data has been received from the defect detection system.

If there are more defects, a next defect image is received from the inspection system in operation 122. It may then be determined whether the defect matches any existing seed defect groups in operation 124. After a plurality of defect images are received and analyzed for matches, a plurality of different seed groups may have been generated. In order to obtain a unique solution, the existing seed groups may be analyzed in a temporal order, such as analyzing the last received seed group (or has the last received defect) for a possible match with the last received defect image, and then analyzing the next to the last received seed group, etc., until a match is found.

Each group may have a defined seed defect, such as the first (or last) received defect that was added to such group, against which other newly received defects may be compared. That is, a comparison can be made between the newly received defect image and only the seed defect of a group, rather than each of the defects that have already been grouped into such group. Of course, the comparison may include an analysis of all the defects of each group and a newly received defect image although this technique may be significantly less efficient, at least at today's processing speeds.

The comparison between a newly received defect image and a seed group may be performed in any suitable manner. In one implementation, the comparison includes pre-screening the defects to determine whether they have a similar shape. If the newly received defect and a seed defect have a similar shape, then the two defects are further analyzed to determine whether the two defects match in other ways (e.g., position, shape, size, orientation, etc.). That is, the two defects may be aligned and compared with each other on a pixel-by-pixel basis. The two defects may be defined as matching when they have a difference that is less than a predetermined threshold criteria (e.g., such as a 2×2 residual). However, this threshold may be adjusted using test reticles to determine an optimal threshold so that the defect data is mapped into a relevant number and type of bins (e.g., "real" defects vs. "systematic" defects). The sensitivity for the grouping may be substantially higher than the inspection sensitivity for detecting defects.

If there is a match, the current defect can be added to the matching group in operation 127. Otherwise, a new seed group may be generated for the current defect in operation 126. Thus, a new seed group is formed when an incoming defect does not match any of the existing seed groups' defects. As a result, each seed group will include a plurality of substantially matching defect images.

After all the defects for a particular reticle are matched to particular seed groups, the seed groups may be analyzed for filtering. In one embodiment, the seed groups may be analyzed one at a time. In other embodiments, the seed groups can be analyzed in parallel. In the illustrated example, a first seed group may be obtained in operation 130. This current seed group may then be filtered if the number of defects in this current seed group is greater than a predetermined threshold in operation 132.

Any suitable number of different filtering thresholds may be used. In one implementation, different thresholds are used for the different background patterns of each defect group. That is, the defect and how it relates to the surrounding area is examined to determine which threshold from a plurality of different thresholds to select. For instance, if a group's defect is a point or particle defect surrounded by a mostly blank area (e.g., a zero dimensional or 0D defect), then this defect is likely a "real" particle defect and, the count threshold is set to, in effect, infinity so that all this group's defects are kept, regardless of how high the defect count is. In another example, if the defect is a one dimensional or 1D defect (e.g., such as a line), the count threshold is set to a particular value, X, to distinguish between pattern type defects vs. "real" defects (e.g., or to achieve a probability of 50% that defects in the group are real defects). The count threshold for a 2D defect can be set lower than the count threshold value for a 1D defect. In a specific implementation, the selected threshold, N, is proportional to the $1/\log(A)$, where A is the area of the unique background pattern. In this embodiment, a 0D defect with a plain background would not be filtered since there is no unique background area (i.e., all background pixels are identical). Likewise, a constant background, e.g., for a 0D defect, may be defined as having an area of 1, which results in the count threshold being infinity so that all defects in a 0D defect group are retained. Defects with larger unique background areas result in relatively lower count thresholds.

Different users may easily select different count thresholds for different defect types. For example, different fabrication processes may require different count thresholds to achieve relevant binning for systematic vs. real defects. Selection of such count thresholds may be accomplished in any suitable manner, such as via a configuration file or a graphical user interface.

After a particular seed group is analyzed for whether to filter the defects of such group from the defect data, it may then be determined whether there are any other seed groups in operation 134. If there are no more seed groups, the procedure 120 ends. Otherwise, the next seed group is obtained in operation 130 and the filtering process continues until all of the seed groups are analyzed for filtering or not filtering.

Figure 2:
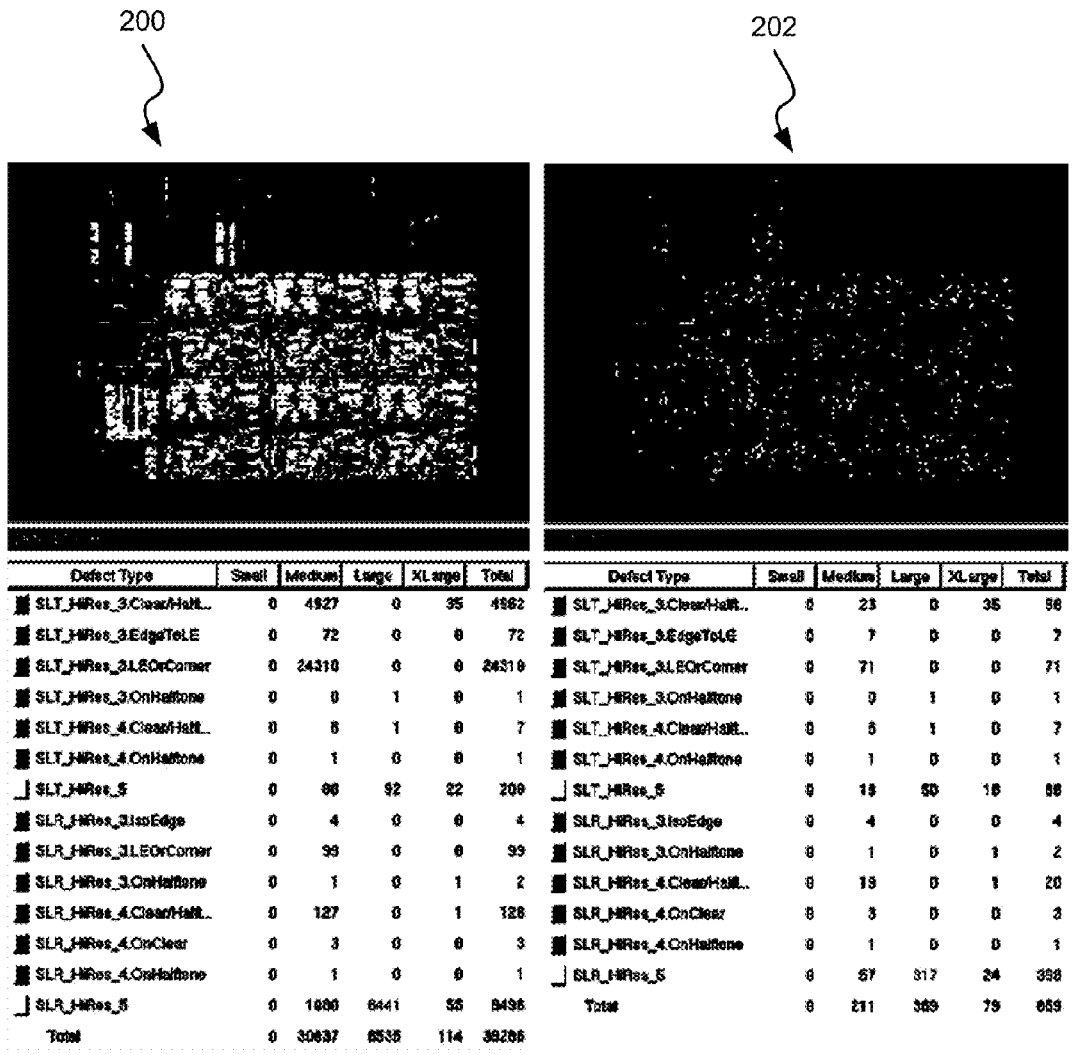
FIG. 2 illustrates the detected defects for a reticle prior to filtering, as compared to the filtered defects for the same reticle.

Certain automatic filtering embodiments can provide a cleaner set of defects for an review tool operator to review. FIG. 2 illustrates the detected defects for a reticle prior to filtering in window 200, as compared to filtered defects for the same reticle in window 202. As shown, the defect count after filtering is substantially reduced. The histograms for each window show the number of defects in each geometric pattern-based defect type: Clear/Halftone, EdgeToLE (edge to line end), LEOrCorner (line edge or corner), OnHalftone, IsoEdge (isolated edge), OnClear, etc., with each according to the size of the defect (small, medium, large, or extra-large). It can be seen that when the systematic filtering is off, the defect map shows a generic multi-die layout due to the existence of systematic defects. When the systematic filtering is turned on, only real defects are left while those systematic defects are filtered out.

Certain embodiments of the above-described techniques include the filtering of false defects according to repeatability and randomness and automatic identification of repeating defects without prior defect templates. These filtering techniques can also overcome a limitation of patch level image processing, which uses parallel processors to process individual "patch" portions of a scanned reticle. Patch level processing, being limited to the confines of a patch, as described further below, is inherently lacking the global view of the defects at the plate level. Certain embodiments of a filtering technique, on the other hand, can make decisions based on the global view of the defects.

Automatic systematic defect filtering can significantly reduce the number of false defects in many cases, in which further recipe optimization and algorithm improvements are difficult to obtain. Systematic defect filtering can also enable a higher sensitivity inspection so as to catch smaller defects, while reducing the need for optimizing the sensitivity settings for specific geometric classifications.

Additionally, certain embodiments may provide a mechanism to automatically filter defects before such defects reach a review station. Since the defect groups that were defined as systematic defects were filtered out, the review operator is only presented with a small subset of defects to review. In contrast, automatic defect classification techniques provide a large number of defect classes, which also include systematic defects. Even though classified defects can allow an operator to review only one defect in each class to determine whether the entire defect class represents critical defects, the operator would also have to tediously review a larger number of defect classes to determine which defect classes included merely systematic defects vs. actual reticle defects. When entire groups are automatically filtered out before operator review, the operator is presented with filtered defects that exclude systematic defects.

Figure 1C:
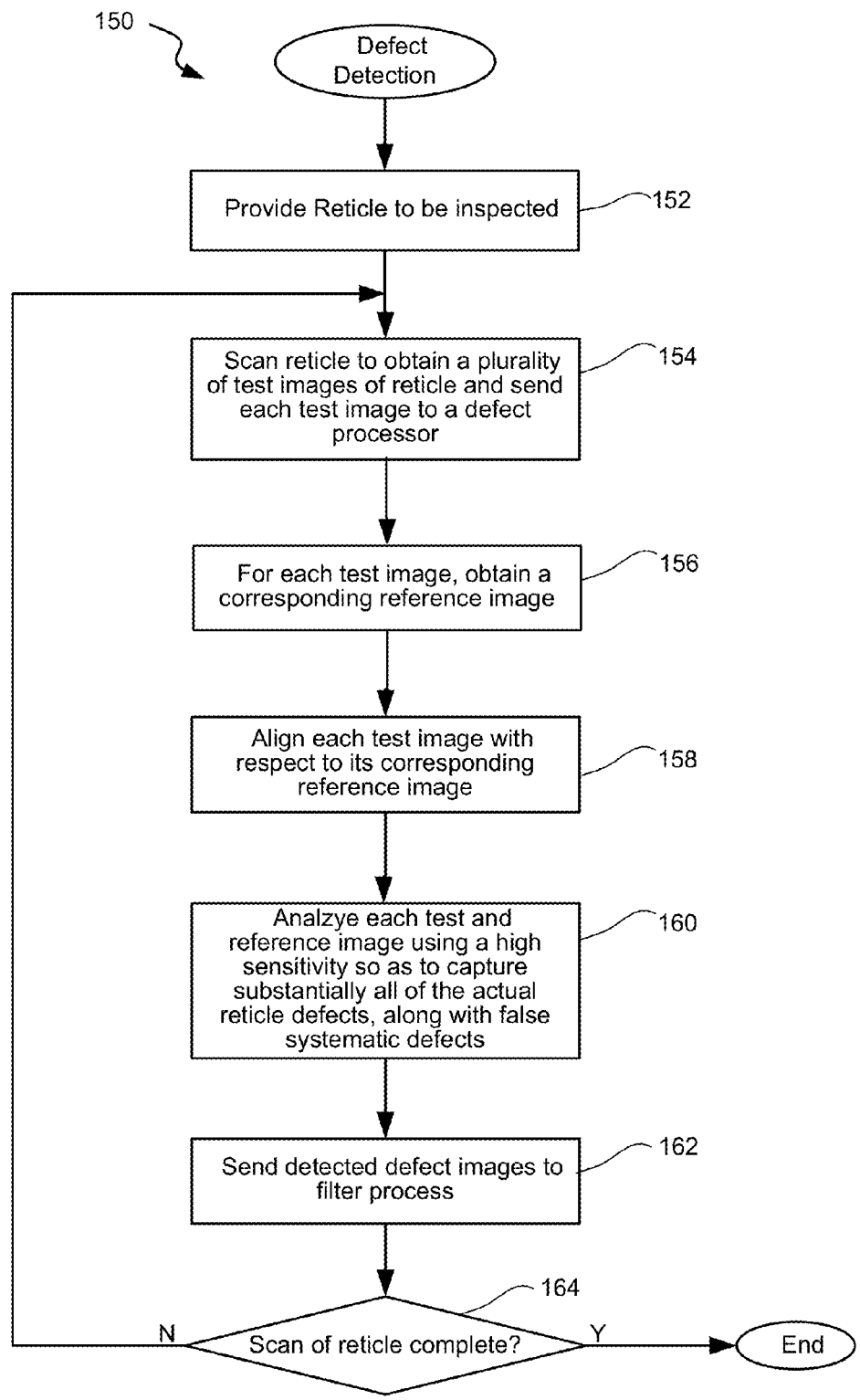
FIG. 1C is a flowchart illustrating one example defect detection procedure.

Any suitable defect detection procedure can be used to input defect data to the automatic systematic defect filtering techniques described herein. FIG. 1C is a flowchart illustrating one example defect detection procedure 150. Initially, a reticle that is to be inspected is provided in operation 152. The reticle may then be scanned to obtain a plurality of test images of the reticle and each test image is sent to a defect processor in operation 154.

Each test image may then be aligned with respect to its corresponding reference image in operation 158. The reference image may be obtained from another reticle image obtained from the reticle itself (e.g., die-to-die) or from the reticle design database (die-to-database) by simulating a reticle fabrication and inspection process on the reticle design patterns. Each test and reference image may also be analyzed using a high-sensitivity so as to capture substantially all of the actual reticle defects, along with false systematic defects, in operation 160.

After each detected image is found, each detected defect image can then be sent to an automatic systematic defect filtering process in operation 162. It may also be determined whether the reticle scan is complete in operation 164. If the reticle scan is complete, the procedure 150 ends. Otherwise, the procedure continues scanning the reticle and detecting defects using a high sensitivity.

Figure 3:
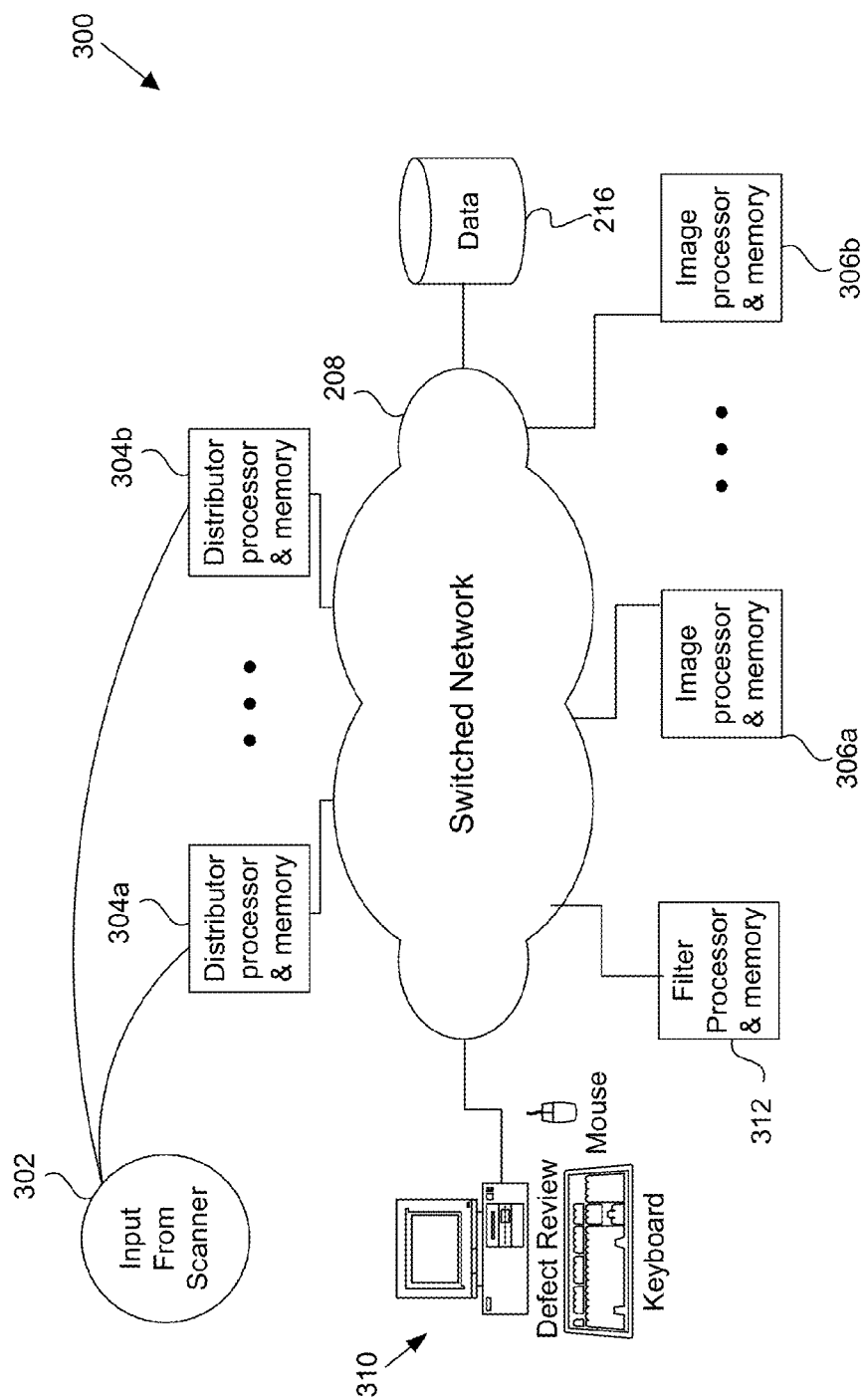
FIG. 3 is a diagrammatic representation of an inspection system in accordance with one embodiment of the present invention.

FIG. 3 is a diagrammatic representation of an inspection system 300 in accordance with one embodiment of the present invention. The inspection system may receive input 302 from an inspection tool or scanner (not shown), a data distribution system (e.g., 304a and 304b), an image processing system (e.g., 306a and 306b), one or more automatic filtering processors and memory (e.g., 312), a network (e.g., switched network 308), an optional mass storage device 316, and one or more inspection control and/or review stations (e.g., 310). Each processor typically may include one or more microprocessor integrated circuits and may also contain interface and/or memory integrated circuits and may additionally be coupled to one or more shared and/or global memory devices.

The inspection system 300 can be arranged to receive input 302 from a scanner or data acquisition system (not shown).

The scanner may be any suitable instrument for obtaining an image of a sample. For example, the scanner may construct an optical image of a portion of the sample based on a portion of light that is reflected, transmitted, or otherwise directed to one or more light sensors. Alternatively, the scanner may utilize an electron beam (e-beam), or other methods, for obtaining an image of the sample.

The image data may be obtained from any suitable sample type. That is, the sample may be anything that results in a relatively large amount of image data. Although the illustrated examples described herein relate to a sample that is in the form of a reticle having a multitude of fine patterns thereon, the techniques of the present invention may also be applied to a sample that takes the form of a semiconductor device or material, a backside pellicle, or a computer disk.

The image data 302 may take any suitable form for representing an image of the sample. For example, the image data typically includes a plurality of images or image portions that each represents a portion or patch of the sample. The portions of the sample can be scanned to create image data. These sample portions and corresponding images may be any size and shape, depending on the particular system and application requirements. The images may be obtained by scanning the sample in any suitable manner. By way of example, the images may be obtained by raster scanning the sample. Alternatively, the images may be obtained by scanning the sample with any suitable pattern, such as a circular or spiral pattern. Of course, the sensors may have to be arranged differently (e.g., in a circular pattern) and/or the sample may be moved differently (e.g., rotated) during scanning in order to scan a circular or spiral shape from the sample.

In the example illustrated below, as the sample moves past the sensors, a rectangular region (herein referred to as a "swath") of the sample is converted into a set of images. In this embodiment, the sensors of the scanner are arranged in a rectangular pattern. For this example, the sensors are arranged to receive light from the sample and generate therefrom a set of data that corresponds to a swath of the sample, which can be, for example, about 1 million pixels wide and about 1000 to 2000 pixels high.

Figure 4:
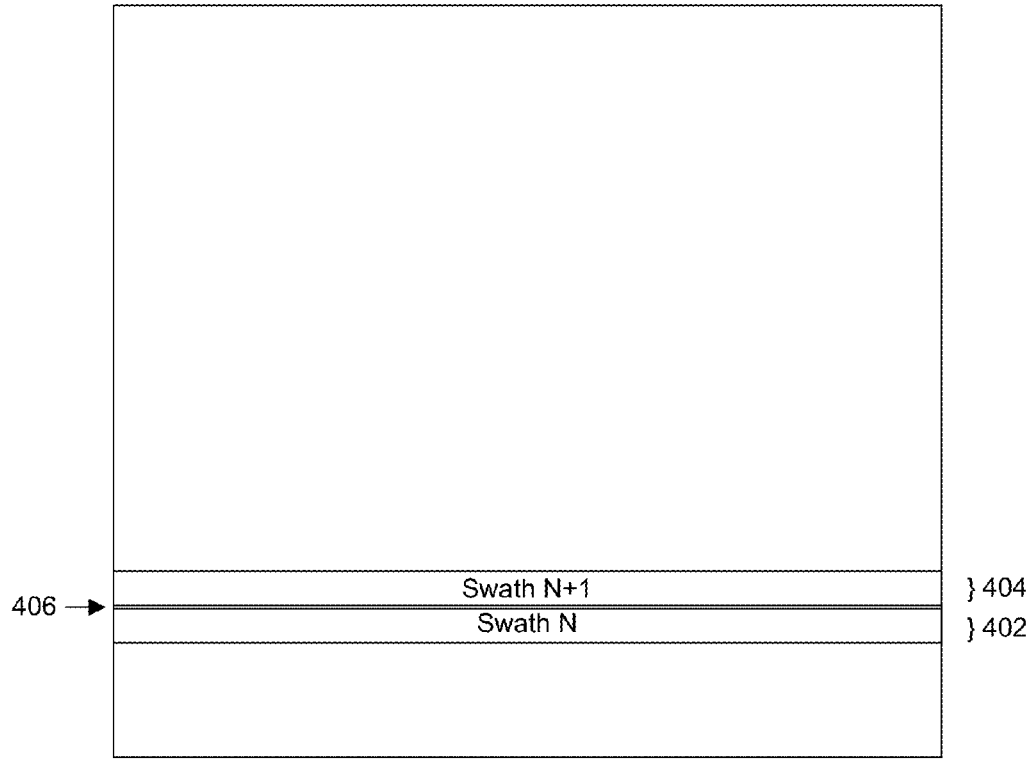
FIG. 4 is a diagrammatic representation of two sets of image data corresponding to two "swaths" of a sample, such as a reticle.
Figure 4:
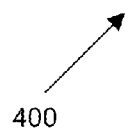

FIG. 4 is a diagrammatic representation of two sets of image data corresponding to two "swaths" 402 and 404 of a sample 400, such as a reticle, in accordance with embodiment of the present invention. Each set of image data may correspond to a "swath" of the sample 400. In the example of FIG. 4, a first set of image data corresponds to a first swath 402 of the sample 400, and a second set of image data corresponds to a second swath 404 of the sample 400.

Each set of image data may be obtained by sequentially scanning swaths from the sample in a serpentine or raster pattern. For example, the first swath 402 of the sample 400 is scanned by an image acquisition system from left to right to obtain a first set of image data. The second swath 404 is then scanned from right to left to obtain a second set of image data.

In a preferred embodiment, there is an overlap 406 between each set of image data and the next set of image data that corresponds to an overlap on the sample. This overlap allows more flexibility in processing certain patterns on the sample 400. For example, this overlap ensures that any pattern anywhere on the part of the surface covered by overlapping swaths will be full contained within at least one swath, as long as the height of the pattern is less than or equal to the height of the overlap area. Most algorithms cannot properly detect a defect in a pattern unless the whole pattern is present in the image portion that the algorithm is examining.

Turning back to FIG. 3, the image data 302 can be received by data distribution system via network 308. The data distribution system may be associated with one or more memory devices, such as RAM buffers, for holding at least a portion of the received image data 302. Preferably, the total memory is large enough to hold an entire swatch of image data. For example, one gigabyte of memory works well for a swatch that is 1 million by 1000 pixels.

The data distribution system (e.g., 304a and 304b) may also control distribution of portions of the received image input data 302 to the image processors (e,g, 306a and 306b). For example, data distribution system may route a first image to image processor 306a, and may route a second image to image processor 306b.

The image processors may receive an image that corresponds to at least a portion or patch of the sample. The image processors may each also be coupled to or integrated with one or more memory devices (not shown), such as DRAM devices that provide local memory functions, such as holding the image data portion. Preferably, the memory is large enough to hold an image that corresponds to a patch of the sample. For example, eight megabytes of memory works well for an image corresponding to a patch that is 512 by 1024 pixels. Alternatively, the image processors may share memory.

Each set of image data 302 may correspond to a swath of the sample. One or more sets of image data may be stored in memory of the data distribution system. This memory may be controlled by one or more processors within the data distribution system, and the memory may be divided into a plurality of partitions. For example, the data distribution system may receive an image corresponding to a portion of a swath into a first memory partition (not shown), and the data distribution system may receive another image corresponding to another swath into a second memory partition (not shown). Preferably, each of the memory partitions of the data distribution system only holds the portions of the image data that are to be routed to a processor associated with such memory partition. For example, the first memory partition of the data distribution system may hold and route a first image to image processor 306a, and the second memory partition may hold and route a second image to image processor 306b.

Figure 5:
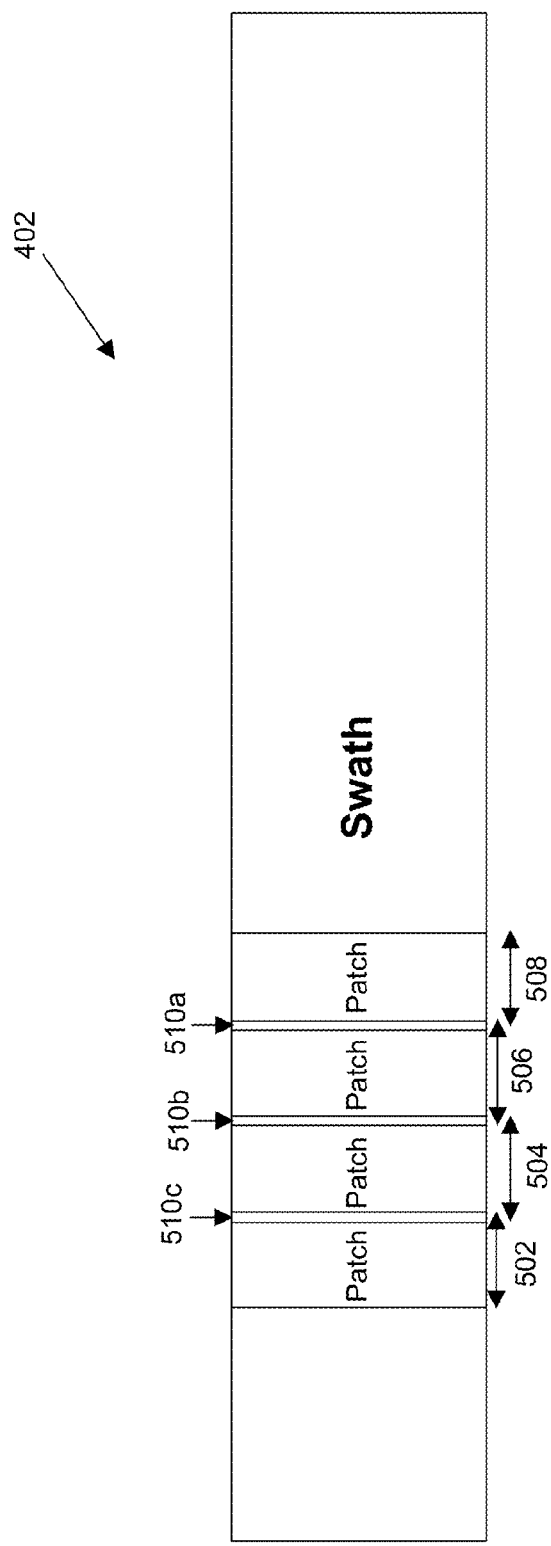
FIG. 5 is a diagrammatic illustration of an image data set that corresponds to a swath that is divided into patches

The data distribution system may also divide and route portions of the received image data to image processors. The image data may be divided by the data distribution system in any suitable manner for facilitating data analysis. For example, the image data may be divided into images that each correspond to a "patch" of the sample. FIG. 5 is a diagrammatic illustration of an image data set 402 that corresponds to a swath that is divided into patches.

As shown, the image set 402 includes a plurality of images 502, 504, 506, and 508, and each image corresponds to patch of a sample. Like the sets of image data corresponding to overlapping swaths, the images within a particular set of image data may also overlap. As shown, there is an overlap area 510c between images 502 and 504, an overlap area 510b between images 504 and 506, and an overlap area 510a between images 506 and 508.

As discussed above for the overlapping swath images, overlapping of patch images also facilitate reliable processing. For example, the overlapping areas make it possible to process a complete structure that lies partly or completely within the overlap area when the width of the structure is less than the overlap width. The erosion or loss of data that occurs at the edges of patches when using convolutions and other local-neighborhood operations can also be eliminated when there is an overlap.

The data distribution system may define and distribute each image of the image data based on any suitable parameters of the image data. For example, the images may be defined and distributed based on the corresponding position of the patch on the sample. In one embodiment, each swath is associated with a range of column positions that correspond to horizontal positions of pixels within the swath. For example, columns 0 through 256 of the swath may correspond to a first patch, and the pixels within these columns will comprise the first image, which is routed to one or more leaf processors. Likewise, columns 257 through 512 of the swath may correspond to a second patch, and the pixels in these columns will comprise the second image, which is routed to different leaf processor(s).

SYSTEM EXAMPLES

Figure 6A:
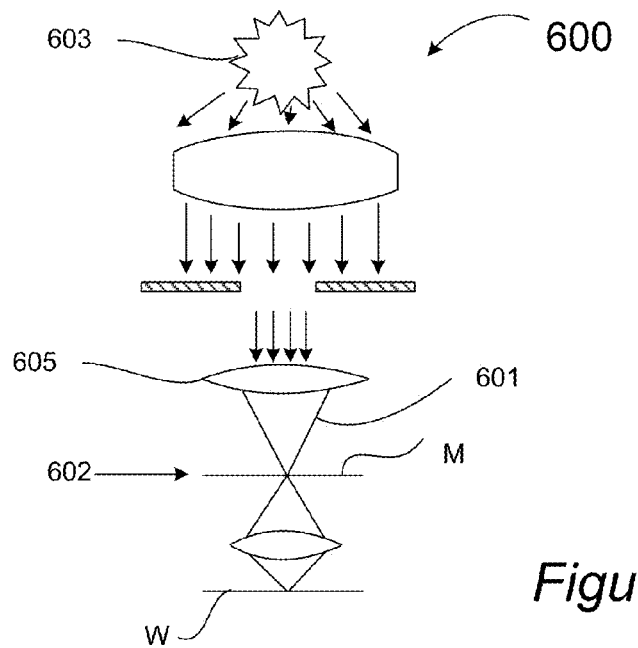
FIG. 6A is a simplified schematic representation of a lithographic system for transferring a mask pattern from a photomask onto a wafer in accordance with certain embodiments.

FIG. 6A is a simplified schematic representation of a typical lithographic system 600 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 603 directs a light beam through an illumination lens 605 onto a photomask M located in a mask plane 602. The illumination lens 605 has a numeric aperture 601 at that plane 602. The value of the numerical aperture 601 impacts which defects on the photomask are lithographic significant defects and which ones are not. A portion of the beam that passes through the photomask M forms a patterned optical signal that is directed through imaging optics 653 and onto a wafer W to initiate the pattern transfer.

Figure 6B:
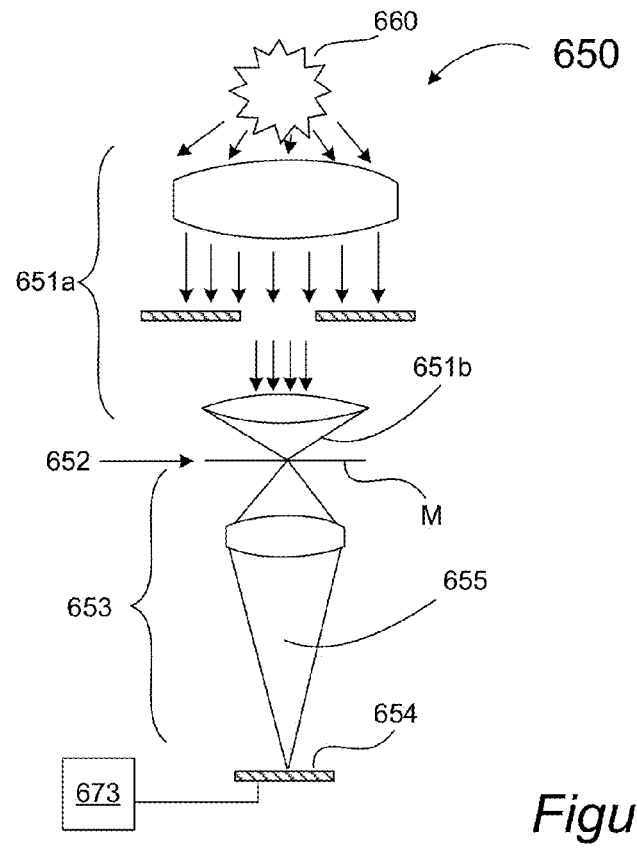
FIG. 6B provides a schematic representation of a photomask inspection apparatus in accordance with certain embodiments.

FIG. 6B provides a schematic representation of an inspection system 650 that has an imaging lens 651a with a relative large numerical aperture 651b at a reticle plane 652 in accordance with certain embodiments. The depicted inspection system 650 includes microscopic magnification optics 653 designed to provide, for example, 60-200× magnification or more for enhanced inspection. The numerical aperture 651b at the reticle plane 652 of the inspection system is often considerable greater than the numerical aperture 601 at the reticle plane 602 of the lithography system 600, which would result in differences between test inspection images and actual printed images.

The inspection techniques described herein may be implemented on various specially configured inspection systems, such as the one schematically illustrated in FIG. 6B. The system 650 includes an illumination source 660 producing a light beam that is directed through illumination optics 651 onto a photomask M in the reticle plane 652. Examples of light sources include lasers or filtered lamps. In one example, the source is a 193 nm laser. As explained above, the inspection system 650 has a numerical aperture 651b at the reticle plane 652 that may be greater than a reticle plane numerical aperture (e.g., element 601 in FIG. 6A) of the corresponding lithography system. The photomask M to be inspected is placed at the reticle plane 652 and exposed to the source.

The patterned image from the mask M is directed through a collection of magnification optical elements 653, which project the patterned image onto a sensor 654. Suitable sensors include charged coupled devices (CCD), CCD arrays, time delay integration (TM) sensors, TDI sensor arrays, photomultiplier tubes (PMT), and other sensors. In a reflecting system, optical elements would direction and capture the reflected image.

The signals captured by the sensor 654 can be processed by a computer system 673 or, more generally, by a signal processing device, which may include an analog-to-digital converter configured to convert analog signals from the sensor 654 into digital signals for processing. The computer system 673 may be configured to analyze intensity, phase, and/or other characteristics of the sensed light beam. The computer system 673 may be configured (e.g., with programming instructions) to provide a user interface (e.g., on a computer screen) for displaying resultant test images and other inspection characteristics. The computer system 673 may also include one or more input devices (e.g., a keyboard, mouse, joystick) for providing user input, such as changing detection threshold. In certain embodiments, the computer system 673 is configured to carry out inspection techniques detailed below. The computer system 673 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM).

Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DU inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:
receiving a stream of defect data from a reticle inspection system, wherein the defect data identifies a plurality of defects that were detected for a plurality of different portions of the reticle;
before reviewing the defect data to determine whether the reticle passes inspection and as the stream of defect data continues to be received, automatically grouping some of the defects with other most recently one or more received defects so as form groups of matching defects;
before reviewing the defect data to determine whether the reticle passes inspection and after all of the defect data for the reticle is received, automatically filtering one or more of the groups of defects that have a number above a predetermined threshold from the defect data so as to form filtered defect data; and
providing the filtered defect data to a review station for determining whether the reticle passes, wherein the predetermined threshold has an adjusted value that depends on a level of uniformity of an area that surrounds the defect of such particular group.

2. The method of claim 1, wherein reviewing the defect data to determine whether the reticle passes inspection is performed manually.

3. The method of claim 1, wherein the defect data is received one defect image at a time and automatically grouping is accomplished by:
as each defect image is received, determining whether such defect image matches an existing seed group if present and adding such defect image to such matching existing seed group, otherwise, forming a new seed group comprising such defect image.

4. The method of claim 3, wherein determining whether each defect image matches an existing seed group if present and adding such defect image to such matching existing seed group is accomplished by comparing such defect image to a plurality of seed groups one at a time until a match is found if present.

5. The method of claim 3, wherein comparing such defect image to a plurality of seed groups one at a time until a match is found if present is accomplished by first determining whether such defect image has a matching shape as a one of the seed groups and only if there is a matching shape, comparing pixel-by-pixel such defect image to the seed group with the matching shape.

6. The method of claim 1, wherein automatically grouping is accomplished in a temporal order of last to first received defect data.

7. The method of claim 1, wherein automatically grouping and filtering is performed without human intervention.

8. The method of claim 1, wherein the predetermined threshold has an adjusted value that is set so that a particular group is not filtered if such particular group's defect is surrounded by a blank background.

9. The method of claim 8, wherein the predetermined threshold has an adjusted value that is higher for a first group that has a 1 dimensional defect than a second group that has a two dimensional defect.

10. The method of claim 1, wherein the predetermined threshold for a particular group's defect type is proportional to $1/\log(A)$, wherein A is an area of unique background pattern.

11. The method of claim 1, wherein the predetermined threshold is selected to result in filtering out one or more of the groups of defects having systematic type defects.

12. A method of inspecting a photolithographic reticle, the method comprising:
receiving a stream of defect data from a reticle inspection system, wherein the defect data identifies a plurality of defects that were detected for a plurality of different portions of the reticle;
before reviewing the defect data to determine whether the reticle passes inspection and as the stream of defect data continues to be received, automatically grouping some of the defects with other most recently one or more received defects so as form groups of matching defects; and
before reviewing the defect data to determine whether the reticle passes inspection and after all of the defect data for the reticle is received, automatically filtering one or more of the groups of defects that have a number above a predetermined threshold from the defect data so as to form filtered defect data;
providing the filtered defect data to a review station for determining whether the reticle passes,
wherein the defect data is received one defect image at a time and automatically grouping is accomplished by as each defect image is received, determining whether such defect image matches an existing seed group if present and adding such defect image to such matching existing seed group, otherwise, forming a new seed group comprising such defect image,
wherein comparing such defect image to a plurality of seed groups one at a time until a match is found if present is accomplished by first determining whether such defect image has a matching shape as a one of the seed groups and only if there is a matching shape, comparing pixel-by-pixel such defect image to the seed group with the matching shape,
wherein it is determined that such defect image is grouped with a particular one of the seed groups when the pixel-by-pixel comparison results in less than a 2 by 2 pixel difference.

13. An inspection system for inspecting a photolithographic reticle, the system comprising at least one memory and at least one processor that are configured to perform the following operations:
receiving a stream of defect data from a reticle inspection system, wherein the defect data identifies a plurality of defects that were detected for a plurality of different portions of the reticle;
before reviewing the defect data to determine whether the reticle passes inspection and as the stream of defect data continues to be received, automatically grouping some of the defects with other most recently one or more received defects so as form groups of matching defects;
before reviewing the defect data to determine whether the reticle passes inspection and after all of the defect data for the reticle is received, automatically filtering one or more of the groups of defects that have a number above a predetermined threshold from the defect data so as to form filtered defect data ; and
providing the filtered defect data to a review station for determining whether the reticle passes,
wherein the predetermined threshold has an adjusted value that depends on a level of uniformity of an area that surrounds the defect of each particular group.

14. The inspection system of claim 13, wherein the defect data is received one defect image at a time and automatically grouping is accomplished by:
as each defect image is received, determining whether such defect image matches an existing seed group if present and adding such defect image to such matching existing seed group, otherwise, forming a new seed group comprising such defect image.

15. The inspection system of claim 14, wherein determining whether each defect image matches an existing seed group if present and adding such defect image to such matching existing seed group is accomplished by comparing such defect image to a plurality of seed groups one at a time until a match is found if present.

16. The inspection system of claim 14, wherein comparing such defect image to a plurality of seed groups one at a time until a match is found if present is accomplished by first determining whether such defect image has a matching shape as a one of the seed groups and only if there is a matching shape, comparing pixel-by-pixel such defect image to the seed group with the matching shape.

17. The method of claim 14, wherein determining whether each received defect image matches an existing seed group if present and adding such received defect image to such matching existing seed group is accomplished by comparing such defect image to a particular seed defect from each of a plurality of seed groups one at a time until a difference between a one of the existing seed group's particular seed defect and such received defect image is less than a predefined second threshold.

18. The method of claim 17, wherein the predefined second threshold is selected using one or more test reticles so that the received defect images are matched to a particular number of different seed groups having different defect types.

19. The method of claim 17, wherein the particular seed defect from each seed group is received last into such each seed group.

20. The inspection system of claim 13, wherein automatically grouping is accomplished in a temporal order of last to first received defect data.

21. The inspection system of claim 13, wherein the predetermined threshold has an adjusted value that is set so that a particular group is not filtered if such particular group's defect is surrounded by a blank background.

22. The inspection system of claim 21, wherein the predetermined threshold is higher for a first group that has a 1 dimensional defect than a second group that has a two dimensional defect.

23. The method of claim 13, wherein the predetermined threshold for a particular group's defect type is proportional to 1/log(A), wherein A is an area of unique background pattern.

24. The inspection system of claim 13, wherein automatically grouping and filtering is performed without human intervention.

25. An inspection system for inspecting a photolithographic reticle, the system comprising at least one memory and at least one processor that are configured to s perform the following operations:
  receiving a stream of defect data from a reticle inspection system, wherein the defect data identifies a plurality of defects that were detected for a plurality of different portions of the reticle;
  before reviewing the defect data to determine whether the reticle passes inspection and as the stream of defect data continues to be received, automatically grouping some of the defects with other most recently one or more received defects so as form groups of matching defects;
  before reviewing the defect data to determine whether the reticle passes inspection and after all of the defect data for the reticle is received, automatically filtering one or more of the groups of defects that have a number above a predetermined threshold from the defect data so as to form filtered defect data ; and
  providing the filtered defect data to a review station for determining whether the reticle passes,
  wherein the defect data is received one defect image at a time and automatically grouping is accomplished by as each defect image is received, determining whether such defect image matches an existing seed group if present and adding such defect image to such matching existing seed group, otherwise, forming a new seed group comprising such defect image,
  wherein comparing such defect image to a plurality of seed groups one at a time until a match is found if present is accomplished by first determining whether such defect image has a matching shape as a one of the seed groups and only if there is a matching shape, comparing pixel-by-pixel such defect image to the seed group with the matching shape,
  wherein it is determined that such defect image is grouped with a particular one of the seed groups when the pixel-by-pixel comparison results in less than a 2 by 2 pixel difference.

26. A non-transitory computer readable medium having instruction stored thereon for performing the following operations:
  receiving a stream of defect data from a reticle inspection system, wherein the defect data identifies a plurality of defects that were detected for a plurality of different portions of the reticle;
  before reviewing the defect data to determine whether the reticle passes inspection and as the stream of defect data continues to be received, automatically grouping some of the defects with other most recently one or more received defects so as form groups of matching defects;
  before reviewing the defect data to determine whether the reticle passes inspection and after all of the defect data for the reticle is received, automatically filtering one or more of the groups of defects that have a number above a predeterbmined threshold from the defect data so as to form filtered defect data; and
  providing the filtered defect data to a review station for determining whether the reticle passes,
  wherein the predetermined threshold has an adjusted value that depends on a level of uniformity of an area that surrounds the defect of each particular group.

* * * * *